United States Patent
Steigerwald

(10) Patent No.: US 8,652,035 B2
(45) Date of Patent: Feb. 18, 2014

(54) VAGINAL CUFF CLOSURE SYSTEMS, AND RELATED METHOD FOR KNOT-FREE LAPAROSCOPIC HYSTERECTOMY

(76) Inventor: James J. Steigerwald, Colorado Springs, CO (US)

( * ) Notice: Subject to any disclaimer, the term of this patent is extended or adjusted under 35 U.S.C. 154(b) by 257 days.

(21) Appl. No.: 13/035,729

(22) Filed: Feb. 25, 2011

(65) Prior Publication Data

US 2011/0301424 A1    Dec. 8, 2011

Related U.S. Application Data

(60) Provisional application No. 61/352,057, filed on Jun. 7, 2010.

(51) Int. Cl.
*A61B 1/32* (2006.01)

(52) U.S. Cl.
USPC .......................................... 600/222; 600/235

(58) Field of Classification Search
CPC ............................................. A61B 2017/0225
USPC .................................. 600/220–223, 184, 235
See application file for complete search history.

(56) References Cited

U.S. PATENT DOCUMENTS

| | | | | |
|---|---|---|---|---|
| 5,460,165 | A * | 10/1995 | Mayes | 600/186 |
| 6,036,638 | A * | 3/2000 | Nwawka | 600/186 |
| 6,432,048 | B1 * | 8/2002 | Francois | 600/220 |
| 7,063,664 | B2 * | 6/2006 | Mohajer | 600/186 |
| 7,329,263 | B2 * | 2/2008 | Bonutti et al. | 606/139 |
| 7,654,953 | B2 * | 2/2010 | Borodulin et al. | 600/220 |
| 2005/0124860 | A1 * | 6/2005 | Mohajer | 600/203 |
| 2006/0142784 | A1 * | 6/2006 | Kontos | 606/139 |
| 2006/0235279 | A1 * | 10/2006 | Hawkes et al. | 600/222 |
| 2008/0004497 | A1 * | 1/2008 | Whitehead et al. | 600/184 |
| 2010/0114032 | A1 * | 5/2010 | Widenhouse et al. | 604/167.03 |
| 2010/0204548 | A1 * | 8/2010 | Bonadio et al. | 600/201 |
| 2011/0105850 | A1 * | 5/2011 | Voegele et al. | 600/207 |

* cited by examiner

*Primary Examiner* — Ellen C Hammond
(74) *Attorney, Agent, or Firm* — Lathrop & Gage LLP; Heather Perrin; Dan Cleveland, Jr.

(57) ABSTRACT

A vaginal cuff closure system includes a speculum having a closed rear aspect, a secure suture ring and a fastener for removably attaching the secure suture ring with a blade of the speculum. A related method of using the closure system in knot-free laparoscopic hysterectomy is also disclosed.

5 Claims, 8 Drawing Sheets

VAGINAL CUFF CLOSURE SYSTEMS, AND RELATED METHOD FOR KNOT-FREE LAPAROSCOPIC HYSTERECTOMY

RELATED APPLICATIONS

This application claims priority of U.S. Provisional Patent Application No. 61/352,057, filed 7 Jun. 2010 and incorporated herein by reference.

BACKGROUND

Hysterectomy—the surgical removal of the uterus—is the second most common major operation among women in the United States today, second only to cesarean section. According to the National Women's Health Information Center, over 600,000 American women have a hysterectomy every year, and ⅓ of American women will have a hysterectomy by age 60. The National Women's Health Information Center. Hysterectomy. Frequently Asked Questions [online], U.S. Department of Health and Human Services Office on Women's Health, Jul. 1, 2006 [retrieved on May 4, 2010]. Retrieved from the Internet: <URL: http://www.4women.gov/faq/hysterectomy.htm>.

Hysterectomy may be performed for a variety of reasons, including removal of reproductive system cancers, prophylactic treatment for those with a strong family history of such cancers, treatment for severe and intractable endometriosis and severe fibroids.

Hysterectomy can be performed in several different ways. Abdominal incision, or laparotomy, is the oldest known and most commonly performed technique in the United States, followed by vaginal hysterectomy, where the surgery is performed through the vaginal canal. Laparoscopic hysterectomy, which has been in conventional practice for just over a decade, allows the uterus to be detached from inside the body by laparoscopic instruments, while the doctor views the uterus, fallopian tubes and ovaries through a camera attached to a telescope. For example, in total laparoscopic hysterectomy ("TLH"), surgically separated tissue (i.e., the uterus and cervix) is removed through an incision at the top of the vaginal canal. The vaginal cuff created during hysterectomy—the portion of the vaginal vault remaining open to the peritoneum—is then closed via laparoscopic suturing. Laparoscopic-assisted supracervical hysterectomy ("LASH") employs in-situ morcellation to cut the uterus into small pieces that are removed via the laparoscopic ports, sparing the cervix.

Advantages of laparoscopic hysterectomy over abdominal or vaginal hysterectomy include smaller incisions, less patient discomfort, reduced complications, reduced hospital stay of, on average, one day, and a faster return to normal activity (2 weeks for laparoscopic hysterectomy, as compared to 6 weeks or longer for abdominal hysterectomy). Laparoscopic surgery also reduces blood loss, allowing a surgeon to detach blood vessels to the uterus while viewing them through the laparoscope. The uterus can then be removed more easily through the vagina, and with less blood loss.

Despite the clear advantages of laparoscopic hysterectomy, a significant number of hospitals and surgeons do not promote the surgery over alternative methods. Reasons include reluctance on the part of surgeons to learn laparoscopic techniques and longer operating times associated with laparoscopy.

SUMMARY

One of the more difficult technical aspects of laparoscopic surgery, which is also a contributor to longer operating times, is the tying of intracorporeal knots. Tying knots with laparoscopic instruments inside the body cavity is a difficult and rate-limiting step in many laparoscopic procedures, and mastering this skill involves a long learning curve. The vaginal cuff closure system and related method of knot-free laparoscopic hysterectomy disclosed herein provide a solution to intracorporeal knot tying during laparoscopic hysterectomy.

The term "knot-free", as used herein, refers to freedom from tying intracorporeal finishing knots during laparoscopic hysterectomy. It will be appreciated that in the described inventions, as well as in conventional laparoscopic surgery, suture having a pre-tied end knot (i.e., an end knot tied before the suture is inserted through a laparoscopic port) may be used to prevent the suture from slipping completely through the tissue to be stitched.

In one embodiment, a vaginal cuff closure system includes a speculum having a closed rear aspect, a secure suture ring and a fastener for removably attaching the secure suture ring with a blade of the speculum.

In one embodiment, a method of knot-free laparoscopic hysterectomy includes laparoscopically detaching a patient's uterus, removing the uterus and inserting a vaginal cuff closure system into the patient's vagina. The cuff closure system is advanced until an attached suture securing ring is positioned near the vaginal cuff. The vaginal cuff is laparoscopically sutured, and suture ends threaded through the suture securing ring. The ring is then detached from the fastener, suture is pulled taut to close the vaginal cuff, and the suture securing ring is crimped about the suture, to maintain tension on the suture and closure of the vaginal cuff. Remaining components of the vaginal cuff closure system are then removed from the vagina.

In one embodiment, a laparoscopic instrument for crimping a suture securing ring includes a pair of jaws protruding from the distal end of a shaft. The proximal end of the shaft couples with a handle body having a lever for activating the jaws. Pressing the lever toward the handle body closes the jaws to crimp the suture securing ring and secure in place suture threaded through the ring.

DETAILED DESCRIPTION

Figure 1:
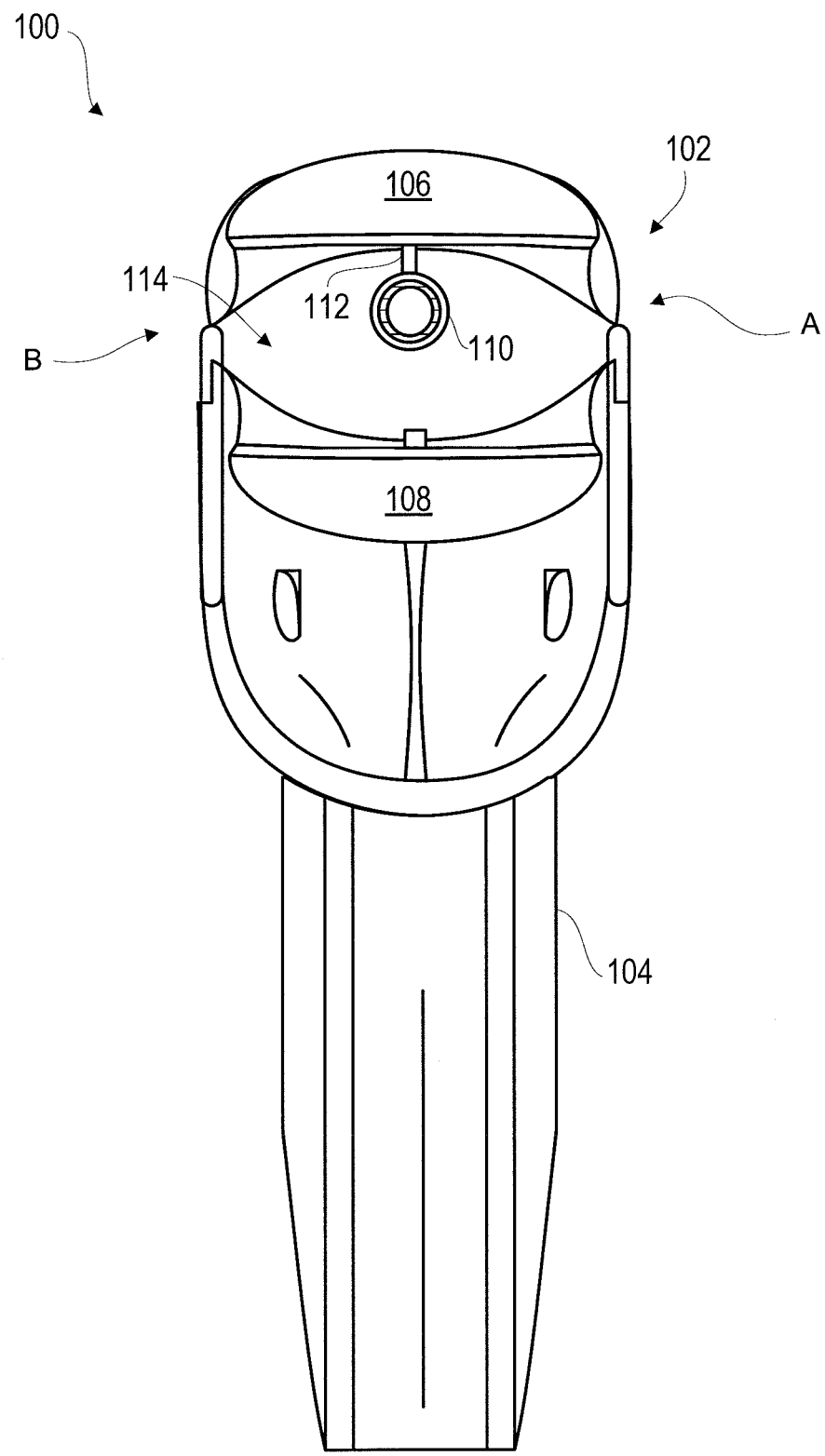
FIG. 1 is a schematic front view of a vaginal cuff closure system, according to an embodiment.
Figure 2:
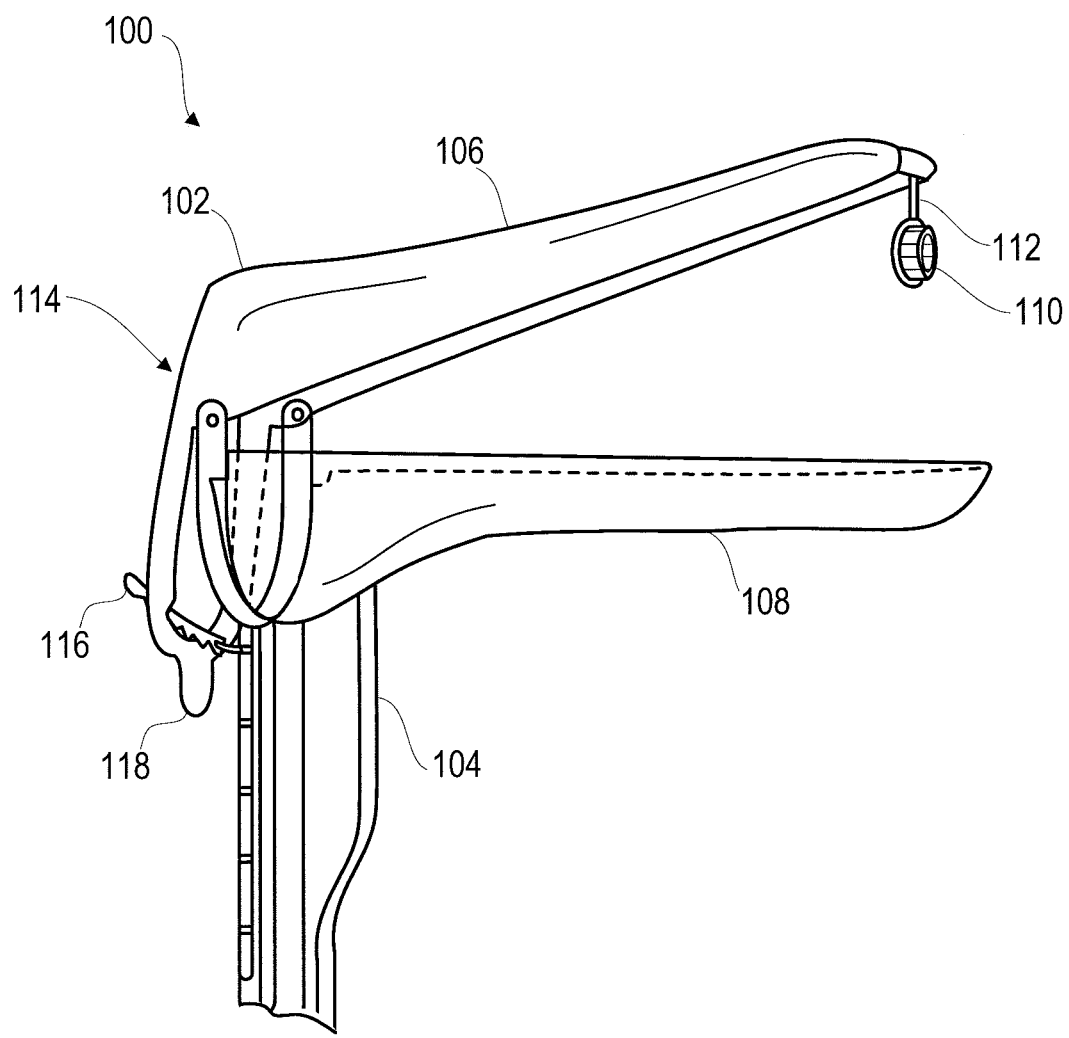
FIG. 2 is a side view of the system of FIG. 1.

FIGS. 1 and 2 show a vaginal cuff closure system 100. System 100, and other systems described herein, may alternately be referred to herein as "vaginal occluders". System 100 includes a speculum 102 having a handle 104 and upper and lower blades 106 and 108. In one embodiment, a suture securing ring 110 (also referred to hereinafter as a secure suture ring 110) removably attaches with a fastener 112 that is formed with or attached to upper blade 106. For example, fastener 112 may be a hook element extruded or otherwise formed with upper blade 106, upon which secure suture ring 110 hangs. Fastener 112 may optionally be a clamp element attached with upper blade 106 and (removably) with secure suture ring 110, or any other means of removably attaching secure suture ring 110 with upper blade 106.

Speculum 102 differs from a conventional vaginal speculum in that the rear aspect (that is, the aspect distal to the patient when the speculum is inserted into the vagina) is closed. Sides of speculum 102 (not shown, but for example between blades 106 and 108) are also at least partially closed. The rear aspect and sides of a conventional vaginal speculum are open, to allow a physician or clinician to view and access the vagina and cervix (e.g., for examination and swabbing) when the speculum is inserted. In one aspect, speculum 102 is manufactured with a closed rear surface 114 between upper and lower blades 106 and 108, and with sealed lateral surfaces A and B between upper and lower blades 106 and 108 (see also FIGS. 4-6 and description thereof for further details regarding closed side surfaces).

Optionally, surface 114 is provided by a separate seal (hereinafter, "seal 114", see also FIG. 3) that is applied to the rear aspect of speculum 102. Seal 114 may be applied to the body of speculum 102 between blades 106 and 108, or seal 114 may overlap blades 106 and 108, either inside or outside of the blades (e.g., mounted with and overlapping inner or outer blade surfaces). Where seal 114 is applied as a step in manufacturing speculum 102, a permanent adhesive may be used. Examples include glue and a permanent double-sided tape or foam tape. Optionally, a reusable adhesive (e.g., reusable silicone adhesive) may be used to secure seal 114 with speculum 102. Sealed side surfaces A and B may likewise be provided by separate seals that can be affixed and removed by a user, when speculum 102 is not manufactured with sealed sides.

In one aspect, seal 114 is sufficiently elastic to allow for opening and closure of blades 106 and 108. Seal 114 is for example made with rubber, flexible plastic, an elastic fabric or any other material having sufficient elasticity to allow blades 106 and 108 their full range of movement when seal 114 attaches with speculum 102.

Seal 114 prevents gas used to inflate the patient's abdomen during laparoscopic surgery (e.g., $CO_2$) from escaping through the vagina. Thus, occluder 100 may be inserted and opened without compromising an intraabdominal work area. Lateral seals A and B enhance maintenance of the work area by flattening against the vaginal walls when speculum 102 is inserted into the vagina, to further prevent escape of surgical gas.

Secure suture ring 110 is a crimpable ring made of biocompatible material (e.g., biocompatible metal). As noted above, secure suture ring 110 removably attaches to fastener 112. Secure suture ring 110 for example includes a collar portion for preventing slippage of the ring and/or for facilitating grasping of ring 110 with laparoscopic tools.

In one example of use, a surgeon performs laparoscopic hysterectomy and removes a patient's uterus through an incision at the top of the vagina. After removal of the uterus, vaginal occluder 100 is inserted blades-first into the vagina, with secure suture ring 110 removably attached to fastener 112. Occluder 100 is advanced until ring 110 is proximate the vaginal incision (e.g., when viewed laparoscopically), and blades 106 and 108 are opened to a desired width and secured in place with locking mechanisms 116 and 118. Mechanisms 116 and 118 are shown in FIG. 2 as a notched catch and thumb-lever element, respectively, although alternate locking mechanisms may be used.

Once vaginal occluder 100 is in place, the surgeon sutures the vaginal incision. In one aspect, loop o-vicryl is used to suture the vaginal cuff in running fashion, starting at opposing lateral edges of the cuff and proceeding medially. In one example, a loop suture is used to close the incision by starting laterally, passing the suture through the anterior and then the posterior part of the incision and then back through the loop, and tightened to anchor the suture at the lateral aspect of the incision. The incision is sewn shut from lateral to medial, stopping in the midline. A second strand of suture and a second needle are used to sew the other side of the incision shut in like manner, lateral to medial. Once suturing is complete, free suture ends are passed through secure suture ring 110, and a laparoscopic instrument is used to release ring 110 from fastener 112. Tension is adjusted on the suture as desired. When the suture is sufficiently tight, the surgeon uses a laparoscopic instrument to crimp secure suture ring 110 about the suture, securing the suture in place. Blades 106 and 108 are returned to fully closed position, and system 100 is removed from the vagina.

Secure suture ring 110 holds the suture in place and at a desired tension without requiring any finishing knots. System 100 therefore allows a surgeon to perform laparoscopic hysterectomy without tying intracorporeal knots, thereby simplifying the procedure and speeding its learning curve while reducing total surgery time. Reduced surgery time leads to reduced anesthesia, both of which in turn translate to reduced costs associated with laparoscopic hysterectomy.

Components 102-108 and 112-114 of vaginal cuff closure system/occluder 100 may be disposable, or they may be sterilized in an autoclave for re-use.

Figure 3:
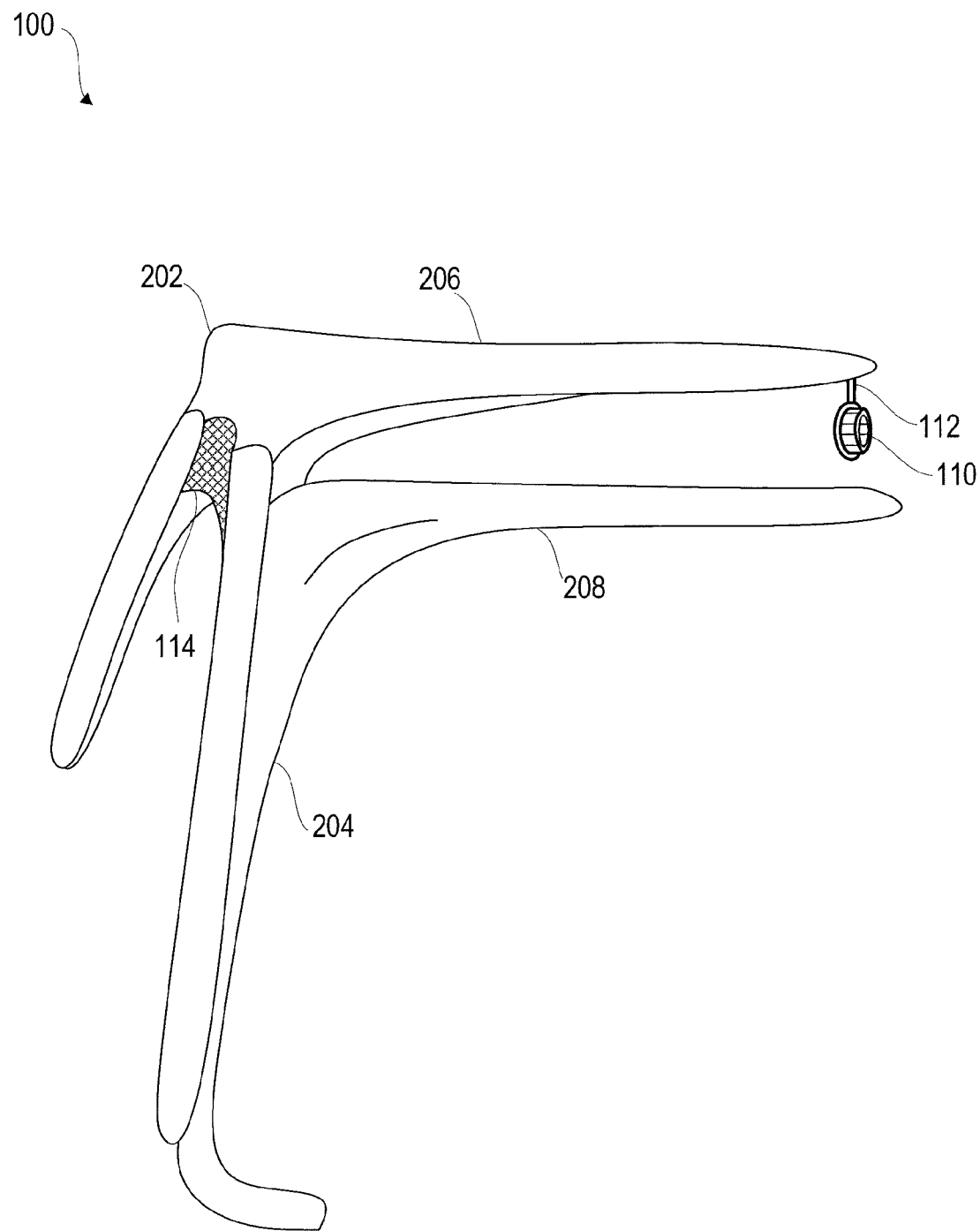
FIG. 3 is a schematic side view of the vaginal cuff closure system of FIGS. 1 and 2, with an alternate speculum body, according to an embodiment.

FIG. 3 shows vaginal occluder 100 with an alternate speculum body 202. It will be appreciated that occluder 100 may incorporate any known speculum type, including Cusco, Grave's, Pederson, Auvard's, Eastman, Sims, Doyen, duckbill, lateral screw type, push-type and middle screw type. Speculum 202 includes a handle 204 with upper and lower blades 206 and 208. Seal 114 closes the rear of speculum 202 and fastener 112 attaches with speculum 202 and ring 110, as is described above with respect to speculum 102.

Figure 4:
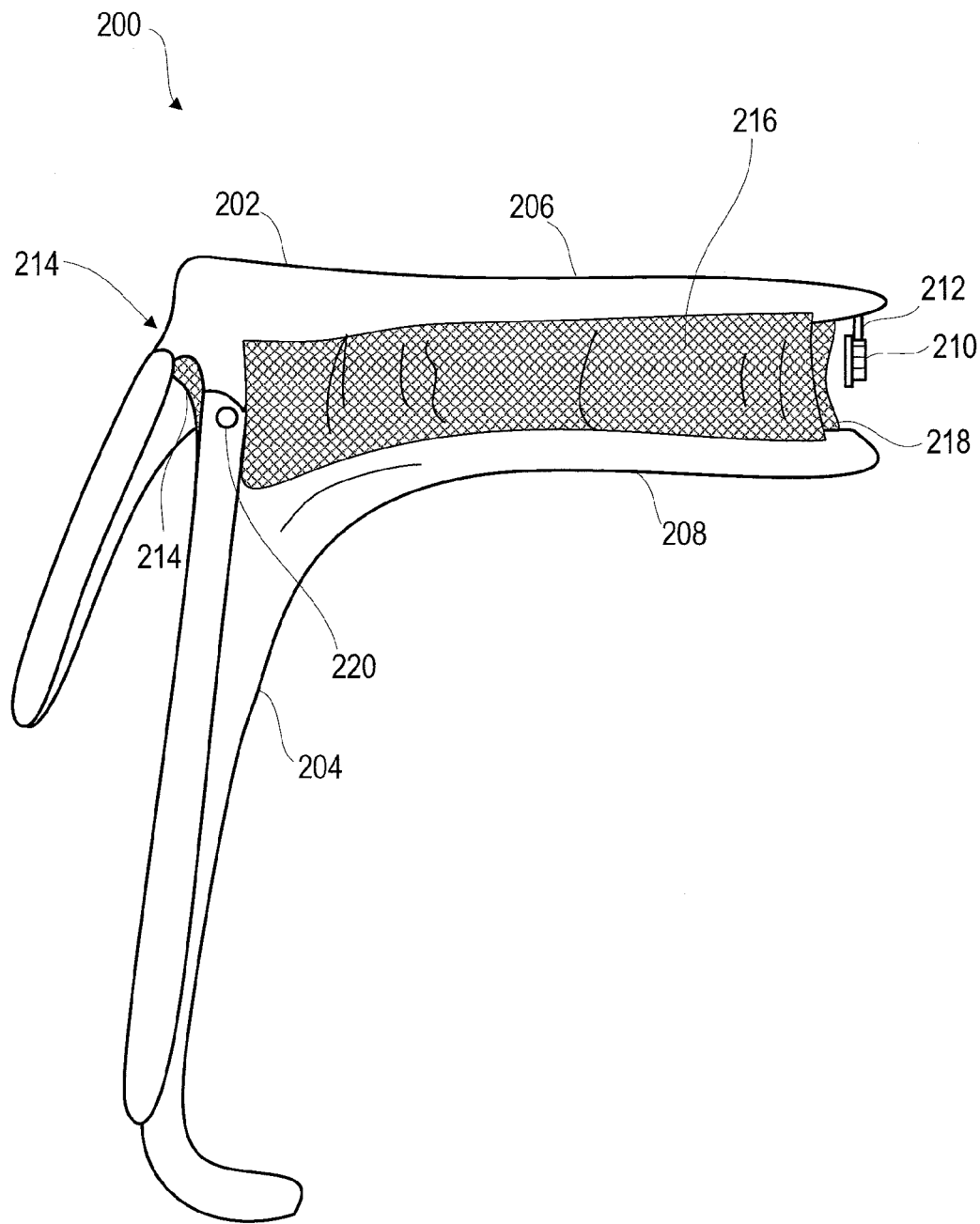
FIG. 4 is a schematic side view of a vaginal cuff closure system having side seals, according to an embodiment.

FIG. 4 shows a vaginal cuff closure system 200, including additional seals for closing the sides of speculum 202 (described above) between blades 206 and 208. It will be appreciated that side seals such as those now described may also complement system 100 (also described above).

System/vaginal occluder 200 includes a pair of side seals 216 and 218, for closing the sides of speculum 202. It will be appreciated that speculum 202 is shown in simplified form, with locking mechanisms removed for clarity of illustration and to provide a better view to an end seal 214. End seal 214 is similar to seal 114, described above. When speculum 202 is inserted into the vagina, side seals 216 and 218 and end seal 214 prevent gas used to distend the abdomen from escaping through the vagina. Side seals 216 and 218 are sufficiently flexible to allow blades 206 and 208 to open and close through their full range of movement. In one aspect, side seals 216 and 218 are permanent or removable rubber latex (or latex-free rubber) sheets affixed between blades 206 and 208, and optionally extending beyond a pivot point 220 for the blades and/or overlapping a portion of handle 204. Side seals 216 and 218 may also be made of flexible plastic, an elastic fabric or any other material having sufficient elasticity to permit full movement of blades 206 and 208.

Figure 5:
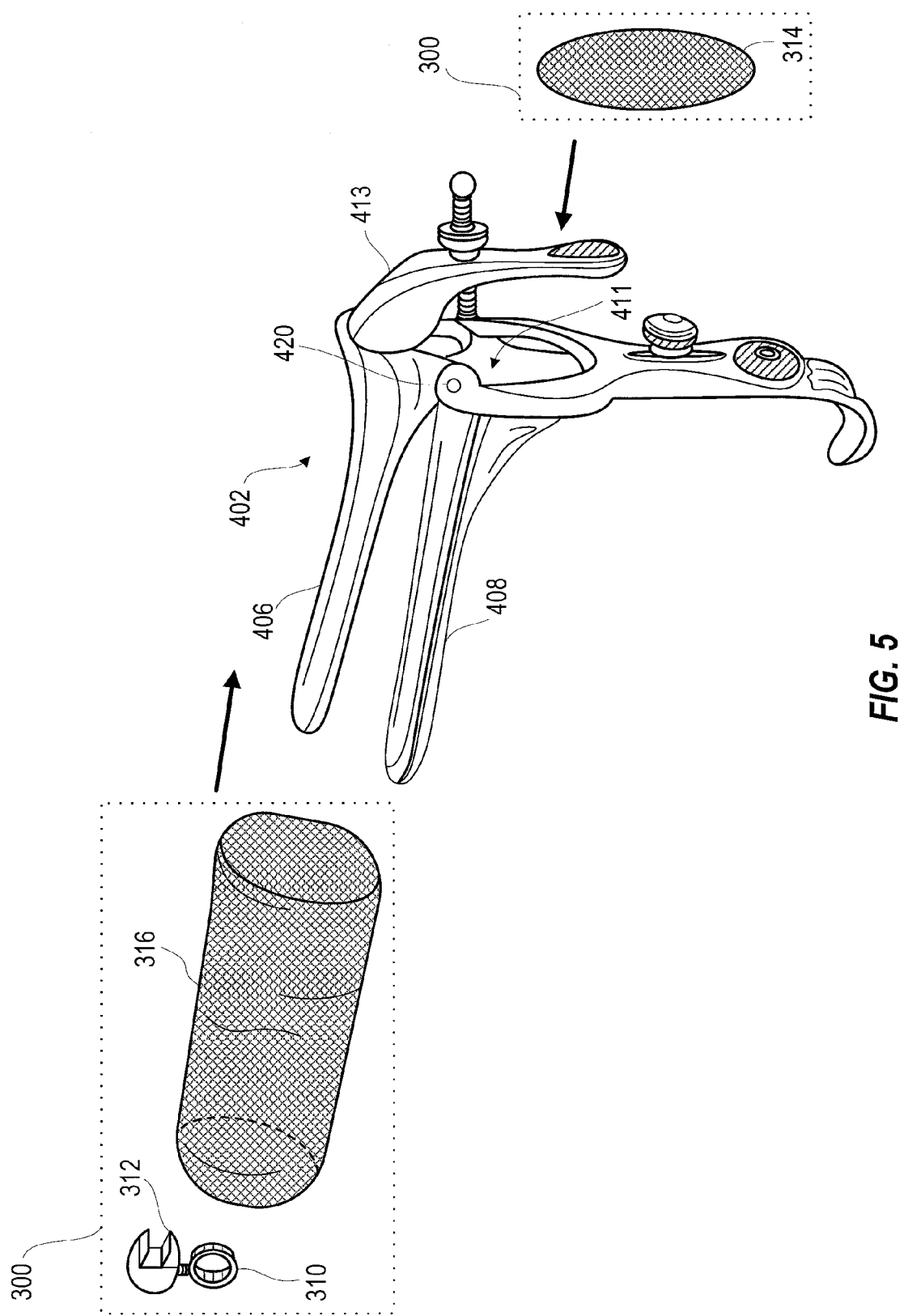
FIG. 5 is a partially exploded, side perspective view of a vaginal cuff closure system for fitting with a conventional speculum, according to an embodiment.

FIG. 5 is a partially exploded drawing showing a vaginal cuff closure system 300. For ease of illustration, components of system 300 are shown enclosed by dotted boxes. System 300 may be retrofitted to a separate speculum 402, for example, one already owned by a surgeon, hospital or clinic.

System 300 includes a secure suture ring 310 for removably attaching with a fastener 312. Like ring 110, ring 310 may include a collar portion for facilitating grasping with a laparoscopic tool, and/or for preventing slippage of ring 110. Fastener 312 is illustratively shown as a clamp for clamping with a top blade 406 of speculum 402; however, alternate fasteners 312 are within the scope hereof.

A flexible sealing sleeve 316 slides over blades 406 and 408 of speculum 402. Sealing sleeve 316 is sufficiently elastic to permit full opening of blades 406 and 408 while maintaining a seal over the open sides between the blades (e.g., that appear or increase when speculum 402 is activated to open blades 406 and 408). A similarly elastic end seal 314 attaches with a rear aspect of speculum 400. In one aspect, end seal 314 includes an adhesive backing for fitting about a rear opening 411 of speculum 402, to seal the opening.

Sleeve 316 and end seal 314 are similar in composition and function to side seals 316 and 218 and end seals 114 and 214, described above. When sleeve 316 and seal 314 are applied to speculum 400 and speculum 402 is inserted into the vaginal canal, sleeve 316 and seal 314 create an air-tight occlusion of the vagina, preventing escape of cavity-inflating $CO_2$ gas.

In one aspect, a release liner is removed from a speculum-contact side (not shown) of end seal 314 to expose an adhesive. Seal 314 is applied over rear opening 411, to seal the opening. The perimeter of seal 314 may for example be pressed to speculum 402, around opening 411, including pressing seal 314 to the base of a thumb lever 413 (or other control or locking structure) to insure that opening 411 is fully covered by seal 314. It will be appreciated that seal 314 is shown having an oval shape for illustrative purposes only, and may instead be shaped to fit with contours of an existing speculum type (e.g., Grave's, Cusco or any other conventional speculum). For example, seal 314 may be provided with a notch or shaped cut-out to fit about the base of thumb lever 413.

Figure 6:
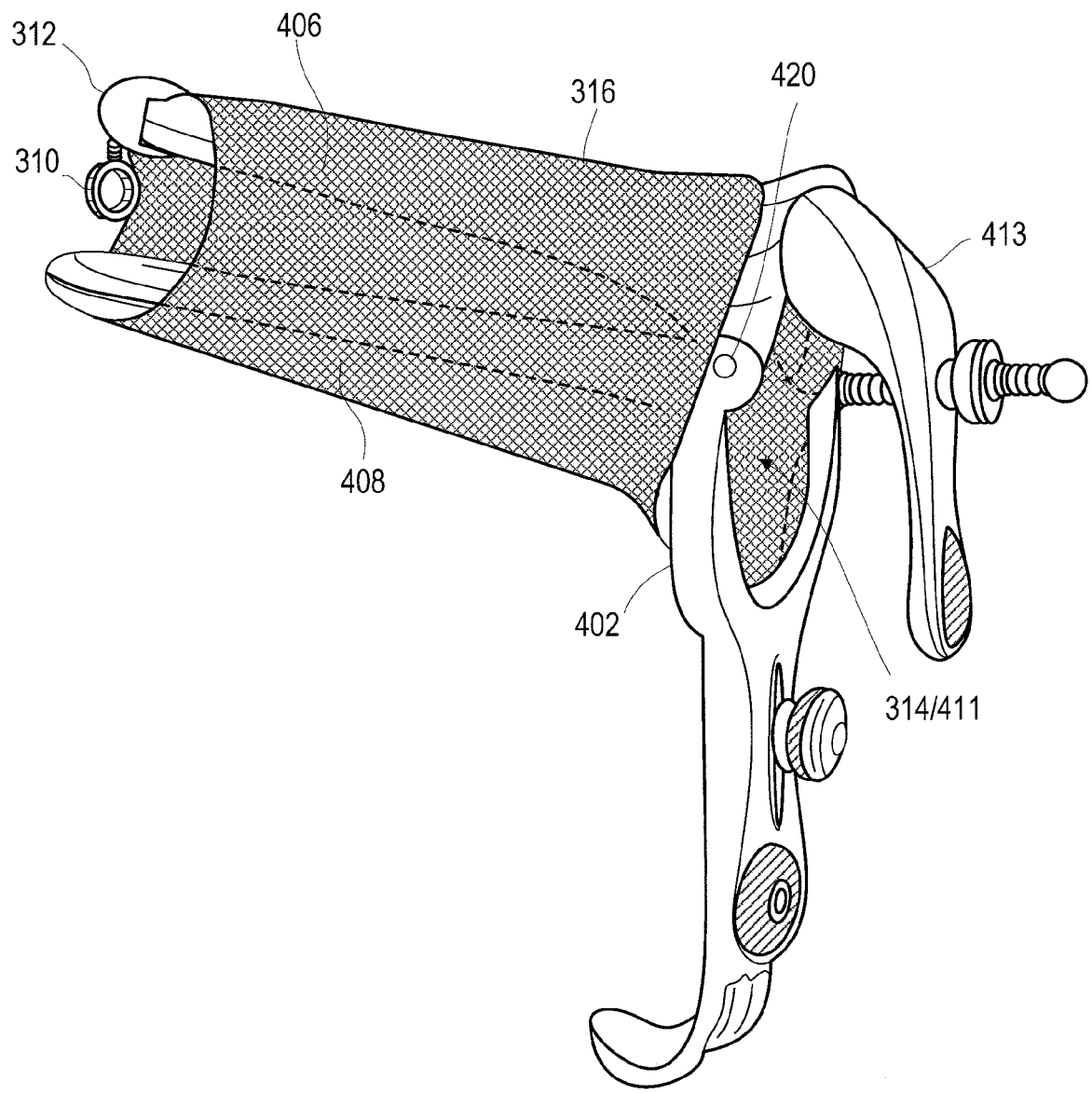
FIG. 6 shows the speculum and vaginal cuff closure system of FIG. 5 fitted together.

Alternately, seal 314 may be applied from within speculum 402 (i.e., from between blades 406 and 408) and secured to inner aspects of blades 406 and 408 and/or the speculum body. Sleeve 316 is advanced over blades 406 and 408 until sufficient coverage is achieved. For example, sleeve 316 may be advanced up to or slightly covering a blade pivot point 420. Once sleeve 316 is in place, fastener 312 is secured at the front of blade 406 (see, e.g., fastener 112 position on blade 106, FIG. 2). Ring 310 may be placed with fastener 312 before or after attachment of fastener 312 and blade 406. Likewise, the other components of system 300 need not necessarily be fitted to speculum 402 in the order described above. FIG. 6 shows speculum 402 fitted with system 300.

Figure 7:
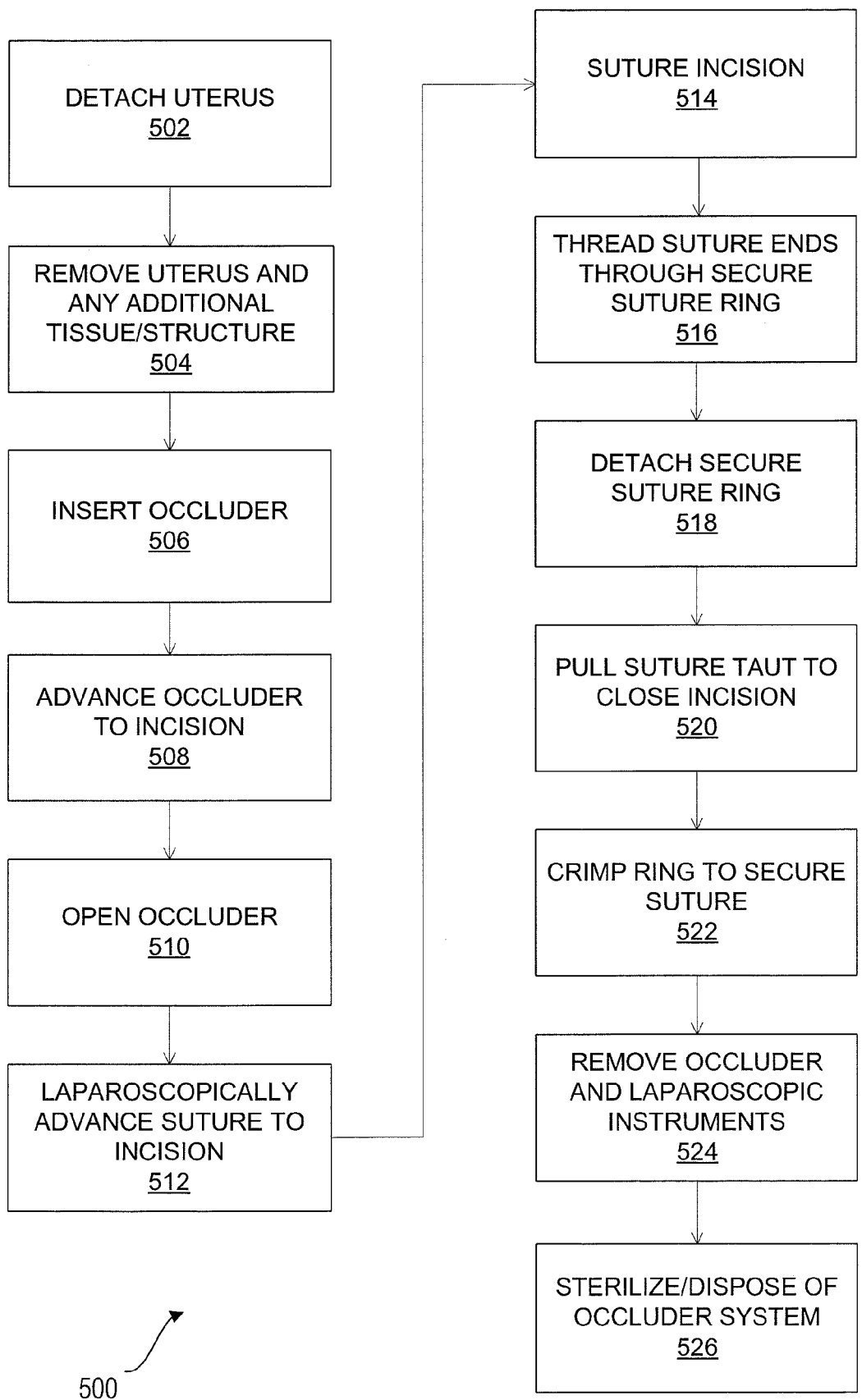
FIG. 7 is a flow chart depicting a method for performing knot-free laparoscopic hysterectomy using any of the systems of FIGS. 1-6.

FIG. 7 illustrates a method 500 for performing knot-free laparoscopic hysterectomy using any of the vaginal occluders/systems described above. FIG. 7 assumes that, if provided as a kit for fitting with a preexisting speculum, the vaginal occluder is assembled prior to commencement of surgery. However, it will be understood that the occluder may alternately be assembled during surgery, before it is needed (i.e., by an assistant). It will also be appreciated that steps of laparoscopic hysterectomy prior to uterine detachment are not described, nor is uterine detachment and removal elaborated below, as these steps are known in the art of gynecological surgery.

In step 502, the uterus is surgically detached using laparoscopic instruments. The uterus and any additional tissue to be removed, such as the cervix and fallopian tubes, are removed through the vagina, in step 504. Following removal, a vaginal occluder is inserted into the vagina and advanced until an attached suture securing ring is proximate the incision in the vagina (vaginal cuff), in steps 506 and 508. The occluder blades are opened as desired, in step 510. Suture is laparoscopically advanced to the vaginal cuff, in step 512, and the cuff is sutured in step 514. Suture ends are threaded through the occluder's suture securing ring, in step 516, and the ring is removed from the fastener holding it to the speculum portion of the occluder, in step 518. Suture is pulled taut to close the vaginal cuff, in step 520. The suture securing ring is then crimped shut over the suture in step 522, to hold the suture securely in place and maintain the desired tautness on the suture, keeping the vaginal cuff closed.

After the vaginal cuff is closed, the occluder is removed from the vagina, and laparoscopic instruments are removed from the abdominal cavity, in step 524. The occluder is disposed of or sterilized in step 526, depending upon whether the occluder is fully disposable or some or all components of the occluder are re-usable.

In one example of steps 506-526, system/occluder 200 is inserted in the vagina and advanced until the surgeon visually confirms that secure suture ring 210 lies just inside the peritoneum. Although not illustrated in FIG. 4, fastener 212 for example includes a thin wire or stiff filament for holding ring 210 slightly forward of speculum 202, such that ring 210 may be advanced just beyond the vaginal cuff and into the peritoneum while speculum 202 and associated components of system 200 remain within the vagina.

Once in place, occluder 200 is opened as desired by the surgeon, for example, to provide additional space for suturing the vaginal cuff. Suture is laparoscopically advanced to the vaginal cuff, and the cuff is then sutured in running fashion starting at angles/sides of the cuff and proceeding to the midline. In one aspect, a loop suture is used to close the incision by starting laterally, passing the suture through the tissue border anterior-to-posterior. Suture is then passed back through the loop and tightened to anchor the suture at the lateral aspect of the incision. The incision is sewn shut from lateral to medial, stopping in the midline. A second strand of suture and a second needle are used to sew the other side of the incision shut, again, lateral to medial. Loose suture ends are then threaded through secure suture ring 210 and ring 210 is detached from fastener 212 using laparoscopic instruments. The suture is pulled taut to close the vaginal cuff, and ring 210 is crimped shut from the abdominal side of the vaginal vault, using a laparoscopic instrument. Occluder 200 is then removed from the vagina without disrupting cuff borders and suture holding the cuff together, as the cuff is sewn shut from the abdominal side while occluder 200 remains in the vagina. Laparoscopic instruments are also removed from the patient's body, and all laparoscopic ports are closed. Occluder system 200 is disposed of or sterilized, as appropriate.

In another example of method 700, system 300 is fitted with re-usable speculum 402. Following surgery, speculum 402 is sterilized in an autoclave and system 300 parts are sterilized or disposed of as appropriate, in step 526.

Figure 8:
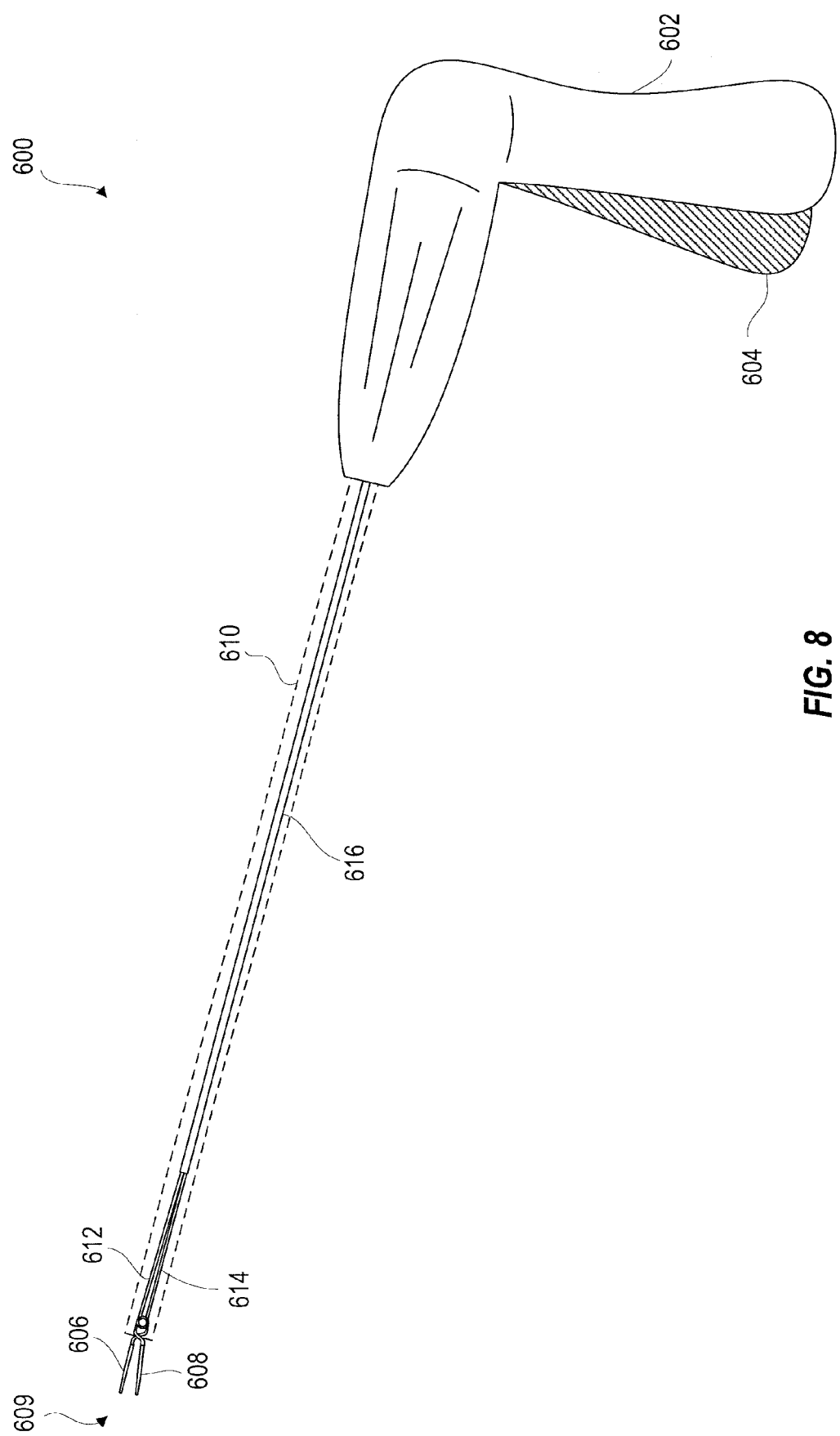
FIG. 8 is a side view of a laparoscopic instrument for crimping a suture securing ring placed using any of the systems of FIGS. 1-6.

FIG. 8 shows a laparoscopic crimping instrument 600 for crimping secure suture ring 110, 210 or 310 of system 100, 200 or 300, respectively. Instrument 600 includes a handle 602 having a lever 604 for activating jaws 606 and 608, which protrude from a distal end 609 of a shaft 610 coupled with handle 602. In one aspect, pressing lever 604 into/towards handle 602 activates wires 612-616 within shaft 610 to effect closure of jaws 606 and 608; however, it will be appreciated that alternate methods of jaw closure known in the art of laparoscopic surgery may also be implemented with instrument 600. Shaft 610 is shown in dotted outline for purposes of illustrating wires 612-614 therein. In one aspect, shaft 610 is approximately 15 inches long.

In practice, distal end 609 is inserted through a laparoscopic trocar (not shown) and instrument 600 is advanced until jaws 606 and 608 contact opposing sides of secure suture ring 110/210/310. Once jaws 606 and 608 grasp ring 110/210/310, lever 604 is pulled inward to close jaws 606 and 608 and crimp secure suture ring 110/210/310 about suture threaded therethrough. Releasing lever 604 opens jaws 606 and 608, freeing the crimped ring from the jaws. After proper closure of ring 110/210/310 is visually confirmed by the surgeon, instrument 600 is withdrawn through the trocar.

While the present invention has been described above, it should be clear that many changes and modifications may be made to the cuff closure system and associated method of knot-free laparoscopic hysterectomy, without departing from the spirit and scope of this invention. For example, all or select parts of the system may be disposable or re-usable. Additionally, system parts shown in one figure may be combined with parts shown in other figures, without departing from the scope hereof. Likewise, although described and shown as being attached with an upper speculum blade, the fasteners and rings disclosed herein may also be attached elsewhere with a speculum (i.e., with a lower blade).

What is claimed is:

1. A vaginal cuff closure system for retrofit assembly with a speculum, comprising:
   a secure suture ring;
   a fastener for removably fitting the secure suture ring with a blade of the speculum;
   an end seal for sealing a rear aspect of the speculum; and
   one or more side sealing mechanisms for sealing left and right sides of the speculum, between upper and lower blades of the speculum;
   wherein the end seal and the one or more side sealing mechanisms comprise an adhesive for securing the end seal and side sealing mechanisms with the speculum to provide an airtight chamber between the speculum blades when the speculum is inserted into a patient's vagina.

2. The system of claim 1, the one or more side sealing mechanisms selected from the group consisting of a flexible sealing sleeve for fitting over the speculum blades, and a pair of flexible side seals.

3. The system of claim 1, the adhesive selected from the group of a re-usable adhesive, a foam tape, a double-sided tape and a glue.

4. The system of claim 1, the secure suture ring comprising a biocompatible material and having a tensile strength sufficient to grasp and secure suture at a desired position and tension when crimped about the suture.

5. The system of claim 4, the secure suture ring comprising a textured internal surface to facilitate grasping of the suture when the ring is crimped about the suture.

* * * * *